(12) United States Patent
Beguin et al.

(10) Patent No.: US 12,708,707 B2
(45) Date of Patent: Aug. 18, 2026

(54) SYSTEM AND METHOD FOR PRESSURE MANAGEMENT FOR A DRUG DELIVERY DEVICE

(71) Applicant: Becton, Dickinson and Company, Franklin Lakes, NJ (US)

(72) Inventors: Steve Beguin, Rathdrum (IE); Michael Yarger, Chapel Hill, NC (US); Simon O'Reilly, Dublin (IE)

(73) Assignee: Becton, Dickinson and Company, Franklin Lakes, NJ (US)

( * ) Notice: Subject to any disclaimer, the term of this patent is extended or adjusted under 35 U.S.C. 154(b) by 716 days.

(21) Appl. No.: 17/527,667

(22) Filed: Nov. 16, 2021

(65) Prior Publication Data

US 2022/0152295 A1 May 19, 2022

Related U.S. Application Data

(60) Provisional application No. 63/114,905, filed on Nov. 17, 2020.

(51) Int. Cl.
*A61M 5/142* (2006.01)

(52) U.S. Cl.
CPC .................. *A61M 5/14244* (2013.01); *A61M 2005/14208* (2013.01); *A61M 2205/3331* (2013.01); *A61M 2205/50* (2013.01); *A61M 2205/8212* (2013.01)

(58) Field of Classification Search
CPC .......... A61M 5/14244; A61M 5/14212; A61M 5/142; A61M 2005/14208
See application file for complete search history.

(56) References Cited

U.S. PATENT DOCUMENTS 4,373,525 A 2/1983 Kobayashi
4,534,756 A 8/1985 Nelson
5,131,816 A 7/1992 Brown et al.
5,215,450 A 6/1993 Tamari
5,328,460 A 7/1994 Lord et al.
5,647,853 A 7/1997 Feldmann et al.
5,803,712 A 9/1998 Davis et al.
5,827,219 A * 10/1998 Uber, III .......... A61M 5/16827 604/30
6,423,035 B1 7/2002 Das et al.
6,485,465 B2 11/2002 Moberg et al.
6,554,791 B1 * 4/2003 Cartledge .......... F04B 43/1253 604/67
6,555,986 B2 4/2003 Moberg
6,595,756 B2 7/2003 Gray et al.
6,656,148 B2 12/2003 Das et al.
(Continued)

FOREIGN PATENT DOCUMENTS

CN 1901953 A 1/2007
CN 102143775 A 8/2011
(Continued)

OTHER PUBLICATIONS

Machine Translation of Beitner (Year: 1985).*

*Primary Examiner* — Laura A Bouchelle
(74) *Attorney, Agent, or Firm* — The Webb Law Firm

(57) ABSTRACT

A drug delivery device includes a power source, a reservoir configured to receive a fluid, a fluid line in fluid communication with the reservoir, a pump configured to deliver a fluid from the reservoir to the fluid line, and a power limitation subsystem configured to limit a power level supplied to the pump.

11 Claims, 12 Drawing Sheets

(56) References Cited

U.S. PATENT DOCUMENTS 6,659,980 B2 12/2003 Moberg et al.
6,923,782 B2 8/2005 O'Mahony et al.
7,193,521 B2 3/2007 Moberg et al.
7,338,260 B2 * 3/2008 Brundle ................ A61M 5/142 417/43
7,621,893 B2 11/2009 Moberg et al.
7,766,873 B2 * 8/2010 Moberg ............ A61M 5/16854 604/131
7,828,528 B2 11/2010 Estes et al.
7,892,206 B2 2/2011 Moberg et al.
7,998,111 B2 8/2011 Moberg et al.
8,065,096 B2 11/2011 Moberg et al.
8,182,447 B2 5/2012 Moberg et al.
8,378,837 B2 2/2013 Wang et al.
8,469,942 B2 6/2013 Kow et al.
8,483,980 B2 7/2013 Moberg et al.
8,647,296 B2 2/2014 Moberg et al.
8,668,672 B2 3/2014 Moberg et al.
8,681,010 B2 3/2014 Moberg et al.
8,715,237 B2 5/2014 Moberg et al.
8,790,294 B2 7/2014 Estes
8,864,739 B2 10/2014 Moberg et al.
8,900,213 B2 12/2014 Pope et al.
9,011,371 B2 4/2015 Moberg et al.
9,033,925 B2 5/2015 Moberg et al.
9,050,406 B2 6/2015 Kow et al.
9,107,999 B2 8/2015 Moberg et al.
9,119,910 B2 9/2015 Wiegel
9,327,073 B2 5/2016 Moberg et al.
9,364,608 B2 6/2016 Moberg et al.
9,433,732 B2 9/2016 Moberg et al.
9,433,733 B2 9/2016 Moberg et al.
9,610,404 B2 4/2017 Rotstein
9,717,849 B2 8/2017 Mhatre et al.
9,731,072 B2 8/2017 Estes
9,879,668 B2 1/2018 Yavorsky et al.
9,895,490 B2 2/2018 Kow et al.
9,962,486 B2 5/2018 Rosinko et al.
9,987,425 B2 6/2018 Alderete et al.
9,993,594 B2 6/2018 Bazargan et al.
10,010,668 B2 7/2018 Tieck
10,219,985 B2 3/2019 Hudson
10,226,573 B2 3/2019 Baek et al.
10,449,292 B2 10/2019 Pizzochero et al.
11,654,220 B2 * 5/2023 Plahey ................ A61M 1/1561 604/28
2004/0133166 A1 7/2004 Moberg et al.
2007/0010702 A1 1/2007 Wang et al.
2008/0221523 A1 9/2008 Moberg et al.
2010/0087778 A1 4/2010 Genosar et al.
2011/0098676 A1 4/2011 Chiang et al.
2013/0041353 A1 2/2013 Shin et al.
2014/0058351 A1 2/2014 Pope et al.
2015/0182697 A1 7/2015 Panzer
2016/0278899 A1 9/2016 Heller et al.
2017/0203036 A1 7/2017 Mazlish et al.
2019/0142699 A1 5/2019 Hudson
2019/0143034 A1 5/2019 Anderson et al.
2020/0069873 A1 3/2020 Pizzochero et al.

FOREIGN PATENT DOCUMENTS

CN 102196833 A 9/2011
CN 102961801 A 3/2013
CN 203790372 U 8/2014
CN 110545862 A 12/2019
CN 210250767 U 4/2020
CN 111905185 A 11/2020
EP 0139225 A1 * 5/1985 ................ H02P 8/12
EP 3072495 B1 * 3/2020 ............. A61J 3/002
JP H06292719 A 10/1994
JP 2005503096 A 1/2005

* cited by examiner

SYSTEM AND METHOD FOR PRESSURE MANAGEMENT FOR A DRUG DELIVERY DEVICE

CROSS-REFERENCE TO RELATED APPLICATION

The present application claims priority to U.S. Provisional Application Ser. No. 63/114,905, filed Nov. 17, 2020, entitled "System and Method for Pressure Management for a Drug Delivery Device", the entire disclosure of which is hereby incorporated by reference in its entirety.

BACKGROUND OF THE INVENTION

Field of the Invention

The present disclosure relates to a device for pressure management for a drug delivery device.

Description of Related Art

Wearable medical devices, such as automatic injectors, have the benefit of providing therapy to the patient at a location remote from a clinical facility and/or while being worn discretely under the patient's clothing. The wearable medical device can be applied to the patient's skin and configured to automatically deliver a dose of a pharmaceutical composition within a predetermined time period after applying the wearable medical device to the patient's skin, such as after a 27 hour delay. After the device delivers the pharmaceutical composition to the patient, the patient may subsequently remove and dispose of the device.

In certain circumstances, due to the medium in which the liquid is being injected, the flow of fluid leaving the device may be impaired, which can lead to increased pressure in the fluid line of the device. When the pressure rises above a certain threshold, the integrity of the fluid path may be compromised causing a leak within the device and a failure to deliver the full dose of medicament. A fluid leak within the device may also cause damage to the device and subsequent system failures as well as potential contamination concerns due to contact between the fluid and the device.

Human subcutaneous tissue is composed of various cell types, extracellular matrix (ECM) constituents, microstructures, and macroscopic arrangement of cells and ECM. Those elements contribute to the mechanical properties of the tissue. The tissue may also include lymphatic system and blood vessels, and has intrinsic fluid absorption and retention properties. These characteristics vary among individuals, location within the body, and over time may cause variable degrees of resistance to the infusion of fluids at the site of injection. When the resistance of the tissue is too high or the absorption rate is too low for a given delivery flow rate from the device, the pressure may build up and reach valves above the threshold where the fluid line and other components may be compromised.

SUMMARY OF THE INVENTION

In one aspect or embodiment, a drug delivery device includes a power source, a reservoir configured to receive a fluid, a fluid line in fluid communication with the reservoir, a pump configured to deliver a fluid from the reservoir to the fluid line, and a power limitation subsystem configured to limit a power level supplied to the pump.

The power limitation subsystem may be a current limiter subsystem. The current limiter subsystem may include PNP transistors or NPN transistors. The drug delivery device may further include a microcontroller, where the power limitation subsystem includes the microcontroller configured to modulate a voltage supplied to the pump. The power limitation subsystem has an activated mode and a deactivated mode.

In a further aspect or embodiment, a method of pressure management for a drug delivery device including a microcontroller, a reservoir, a pump, a fluid line, and a power source, includes: delivering fluid through the fluid line via the pump at a first power level; detecting a pressure within the fluid line; determining whether the pressure within the fluid line exceeds a high pressure threshold level; delivering fluid through the fluid line via the pump at a second power level until a predetermined condition is satisfied, where the second power level is lower than the first power level; and resuming the delivery of the fluid through the fluid line at the first power level after the predetermined condition is satisfied.

The predetermined condition may be a predetermined pressure level within the fluid line. The second power level may be provided via a current limiter subsystem. The current limiter subsystem may include transistors, such as bipolar, MOSFET, or CMOS transistors, an operational amplifier, or other active circuitry. The second power level may be provided by modulating the voltage supplied to the pump. The pressure within the fluid line may be detected by measuring a current of the drug delivery device during actuation of the pump. The measuring of the current of the drug delivery device may include subtracting a reference current value from a peak current value during an actuation cycle of the pump to determine a stroke current value. The power may be controlled by modulating or controlling a level of current or by modulating or controlling a level of voltage.

In a further aspect or embodiment, a computer program product for a method of pressure management for a drug delivery device including a microcontroller, a reservoir, a pump, a fluid line, and a power source, the computer program product including at least one non-transitory computer-readable medium including program instructions that, when executed by the microcontroller, cause the drug delivery device to: deliver fluid through the fluid line via the pump at a first power level; detect a pressure within the fluid line; determine whether the pressure within the fluid line exceeds a high pressure threshold level; deliver fluid through the fluid line via the pump at a second power level until a predetermined condition is satisfied, with the second power level lower than the first power level; and resume the delivery of the fluid through the fluid line at the first power level after the predetermined condition is satisfied.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION OF THE INVENTION

Spatial or directional terms, such as "left", "right", "inner", "outer", "above", "below", and the like, are not to be considered as limiting as the invention can assume various alternative orientations.

All numbers used in the specification and claims are to be understood as being modified in all instances by the term "about". By "about" is meant a range of plus or minus ten percent of the stated value. As used in the specification and the claims, the singular form of "a", "an", and "the" include plural referents unless the context clearly dictates otherwise. The terms "first", "second", and the like are not intended to refer to any particular order or chronology, but instead refer to different conditions, properties, or elements. By "at least" is meant "greater than or equal to".

Figure 1:
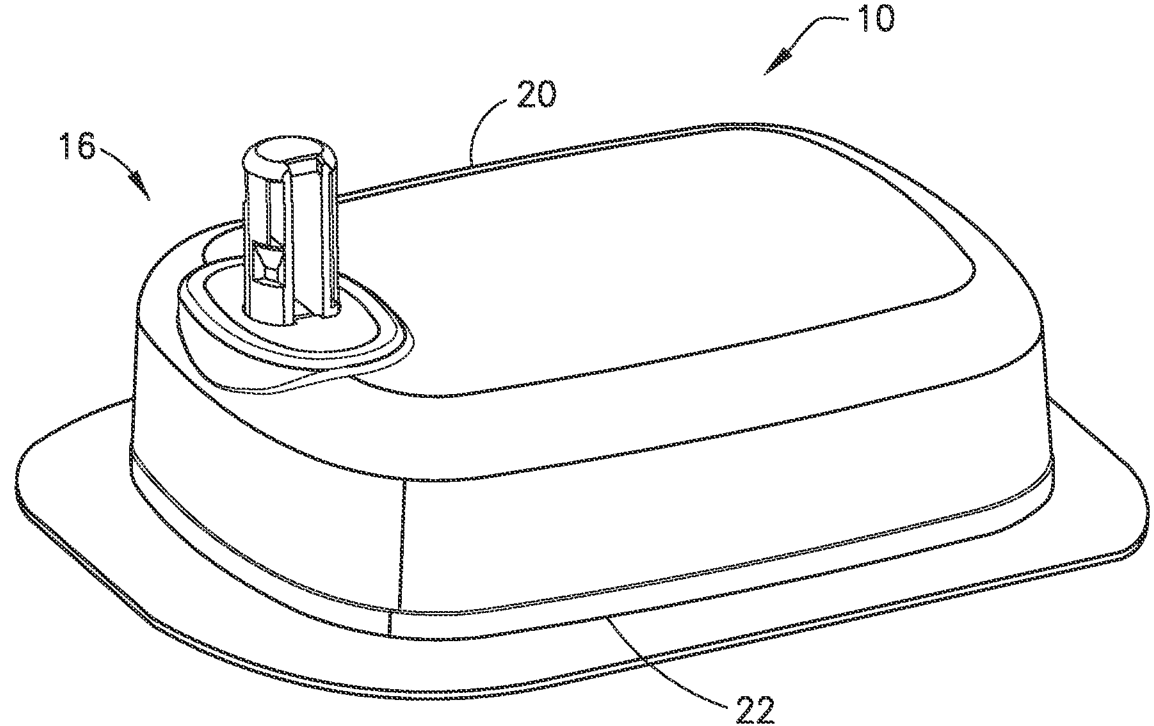
FIG. 1 is a perspective view of a drug delivery device according to one aspect or embodiment of the present application.
Figure 2:
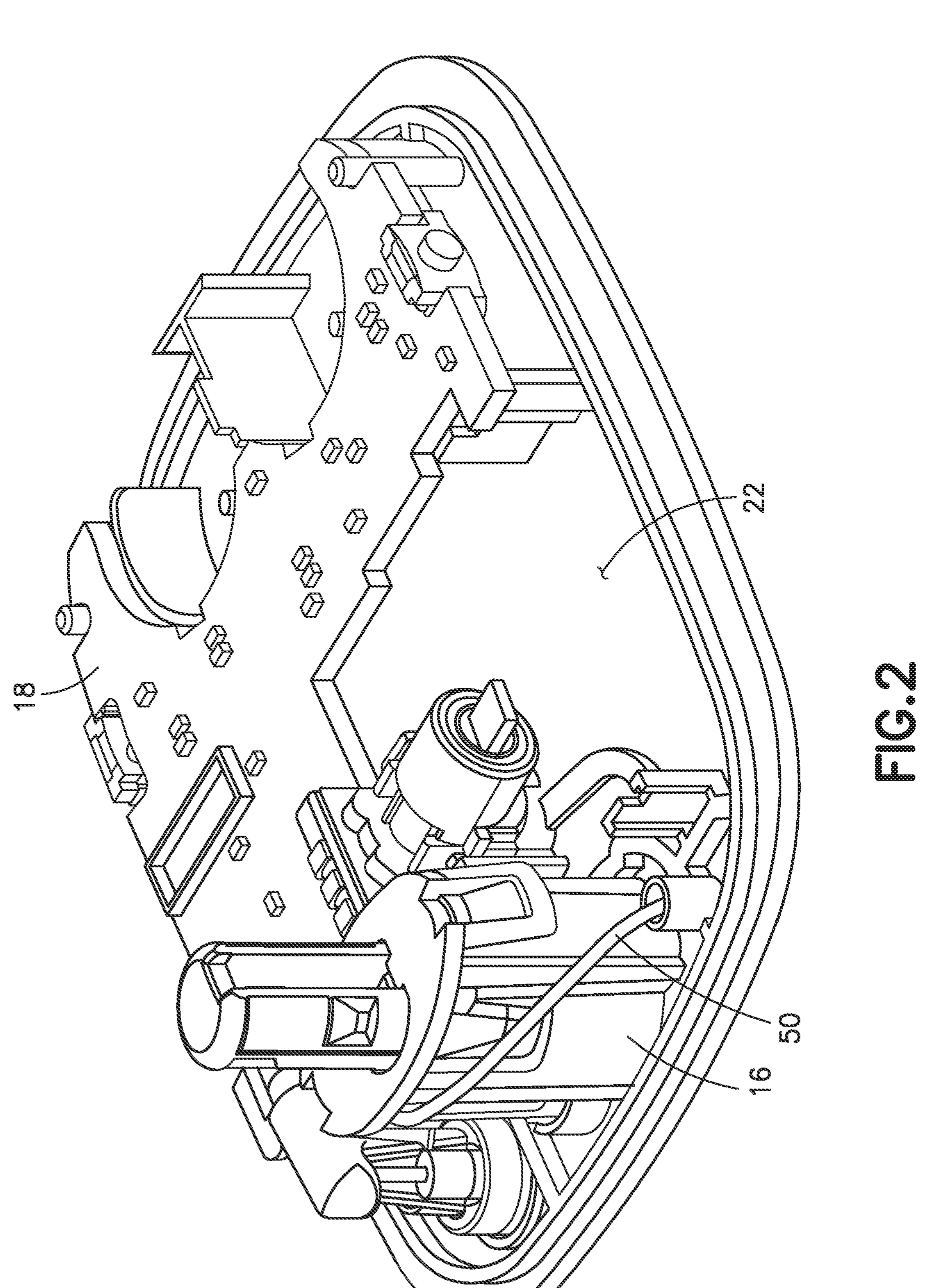
FIG. 2 is a perspective view of the drug delivery device of FIG. 1, with a top cover removed.
Figure 3:
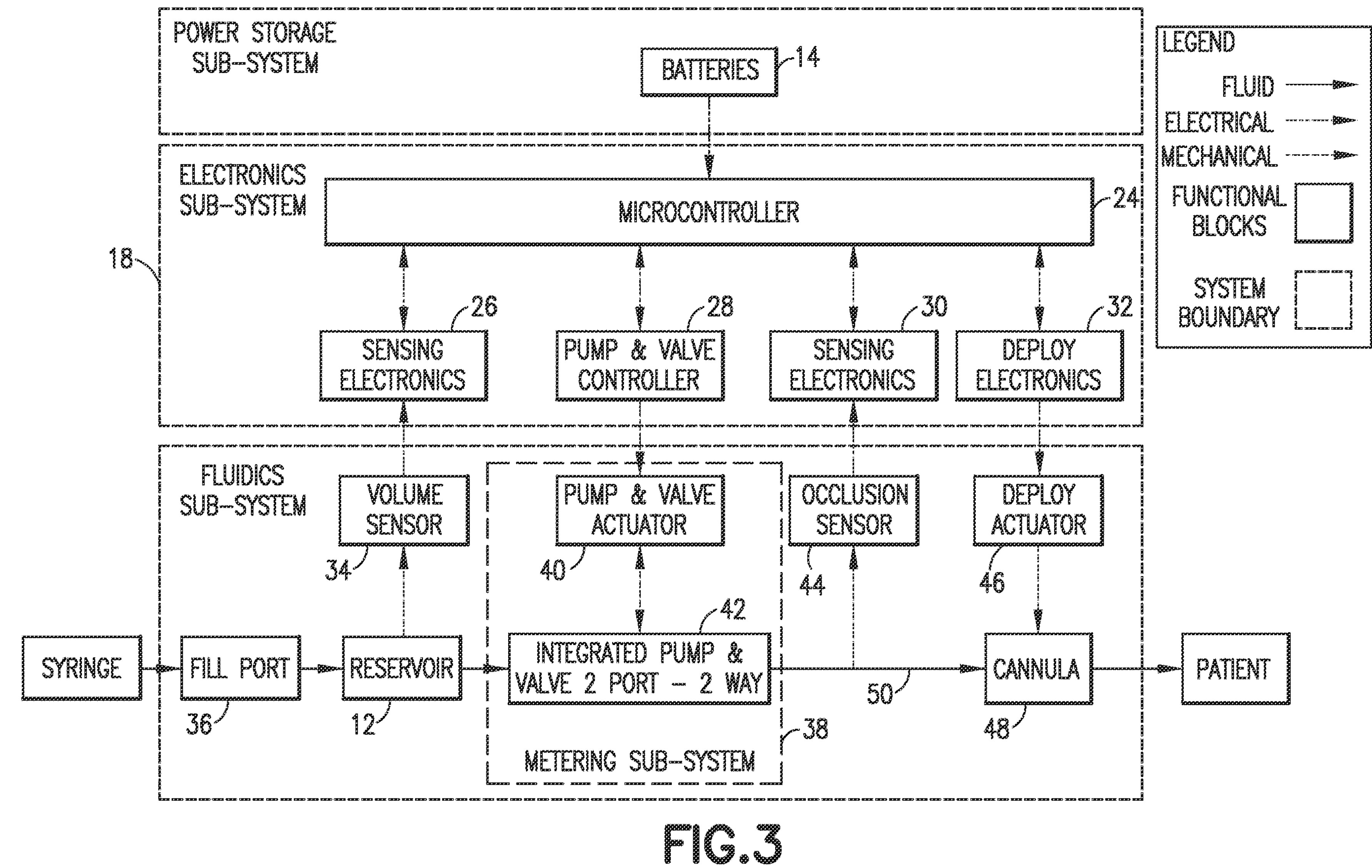
FIG. 3 is a schematic of the drug delivery device of FIG. 1.

Referring to FIGS. 1-3, a drug delivery device 10 includes a reservoir 12, a power source 14, an insertion mechanism 16, control electronics 18, a cover 20, and a base 22. In one aspect or embodiment, the drug delivery device 10 is a wearable automatic injector, such as an insulin or bone marrow stimulant delivery device. The drug delivery device 10 may be mounted onto the skin of a patient and triggered to inject a pharmaceutical composition from the reservoir 12 into the patient. The drug delivery device 10 may be pre-filled with the pharmaceutical composition, or it may be filled with the pharmaceutical composition by the patient or medical professional prior to use.

The drug delivery device 10 is configured to deliver a dose of a pharmaceutical composition, e.g., any desired medicament, into the patient's body by a subcutaneous injection at a slow, controlled injection rate. Exemplary time durations for the delivery achieved by the drug delivery device 10 may range from about 5 minutes to about 60 minutes, but are not limited to this exemplary range. Exemplary volumes of the pharmaceutical composition delivered by the drug delivery device 10 may range from about 0.1 milliliters to about 10 milliliters, but are not limited to this exemplary range. The volume of the pharmaceutical composition delivered to the patient may be adjusted.

Referring again to FIGS. 1-3, in one aspect or embodiment, the power source 14 is a DC power source including one or more batteries. The control electronics 18 include a microcontroller 24, sensing electronics 26, a pump and valve controller 28, sensing electronics 30, and deployments electronics 32, which control the actuation of the drug delivery device 10. The drug delivery device 10 includes a fluidics sub-system that includes the reservoir 12, a volume sensor 34 for the reservoir 12, a reservoir fill port 36, and a metering system 38 including a pump and valve actuator 40 and a pump and valve mechanism 42. The fluidic sub-system may further include an occlusion sensor 44, a deploy actuator 46, a cannula 48 for insertion into a patient's skin, and a fluid line 50 in fluid communication with the reservoir 12 and the cannula 48. In one aspect or embodiment, the insertion mechanism 16 is configured to move the cannula 48 from a retracted position positioned entirely within the device 10 to an extended position where the cannula 48 extends outside of the device 10. The drug delivery device 10 may operate in the same manner as discussed in U.S. Pat. No. 10,449,292 to Pizzochero et al, incorporated herein by reference.

Figure 4:
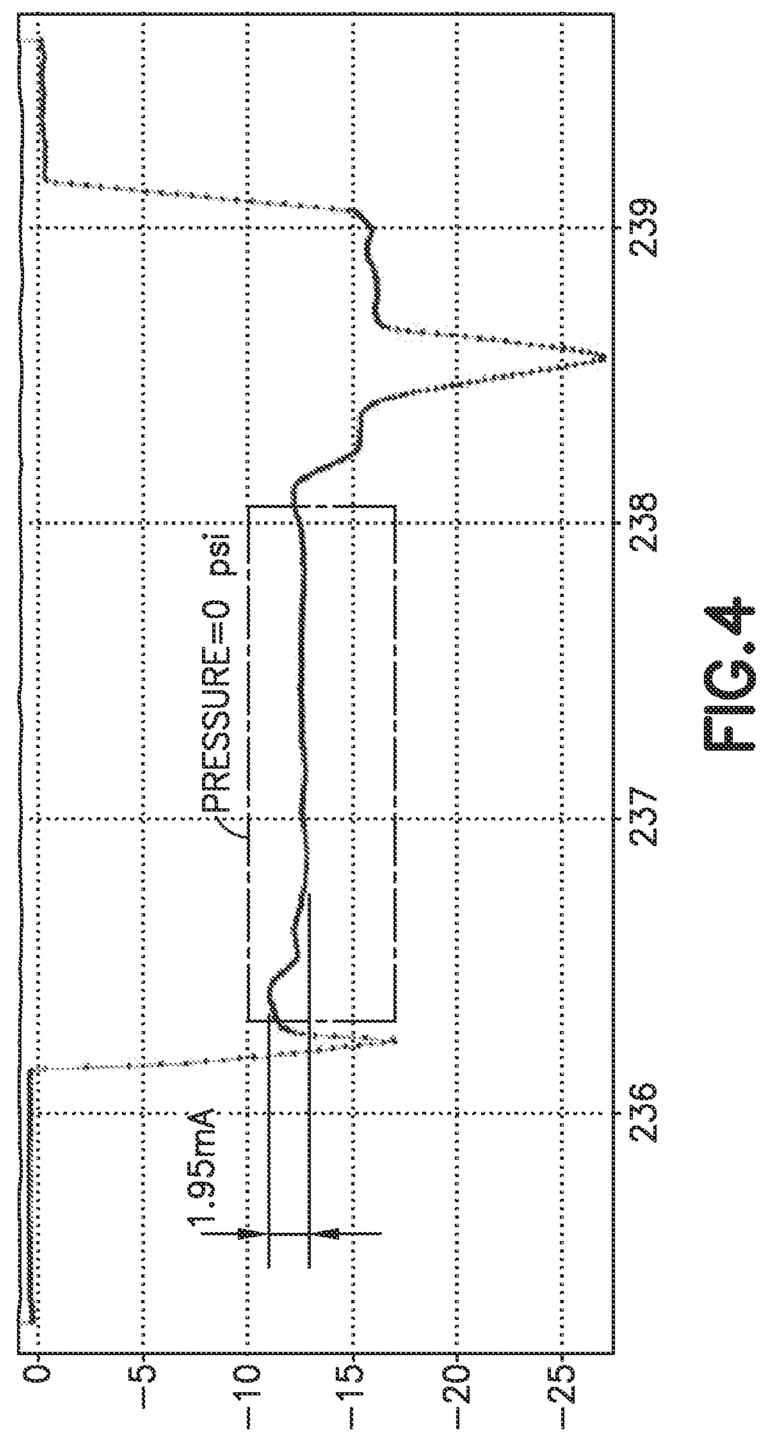
FIG. 4 is a graph of current versus time for the drug delivery device of FIG. 1, showing a 0 psi pressure condition according to one aspect or embodiment of the present application
Figure 5:
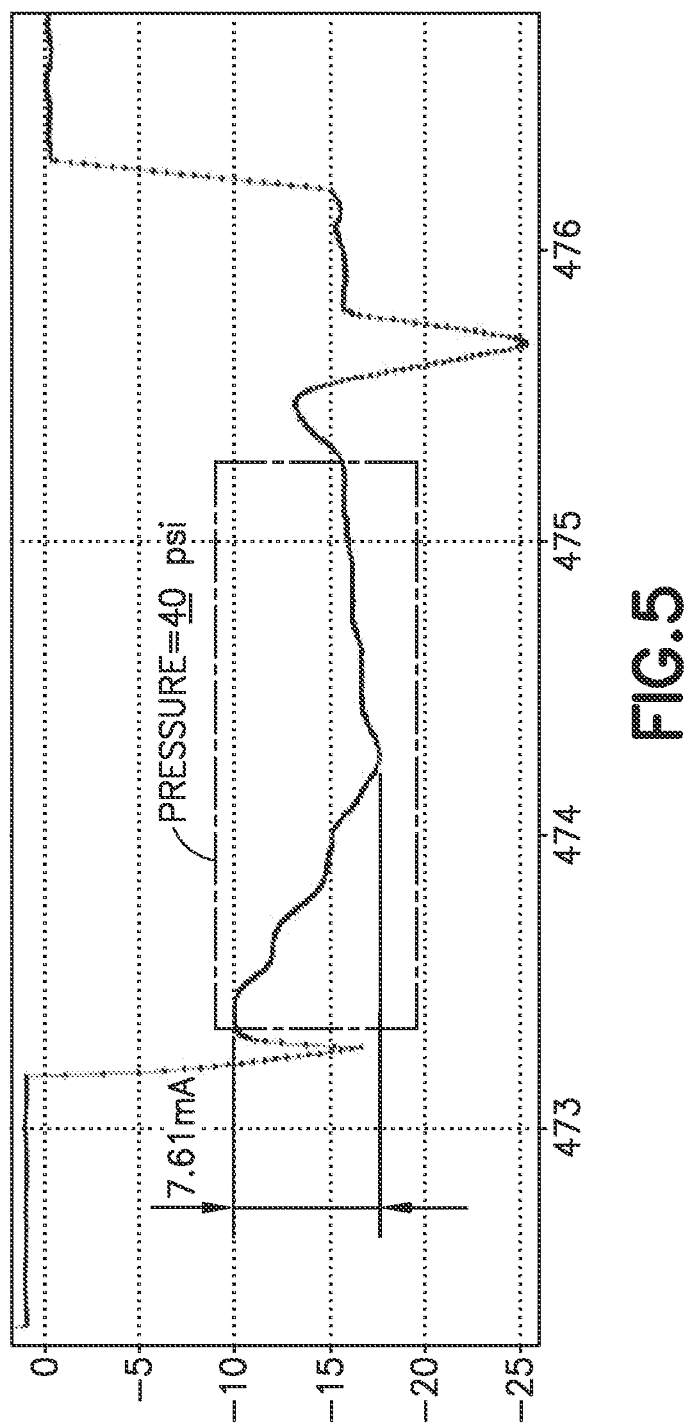
FIG. 5 is a graph of current versus time for the drug delivery device of FIG. 1, showing a 40 psi pressure condition according to one aspect or embodiment of the present application.

Referring to FIGS. 4 and 5, a relationship between pressure within the fluid line 50 and current required to push the pump and valve mechanism 42 forward is shown. The pump and valve mechanism 42 has an aspiration cycle and a dispense cycle with the dispense cycle being shown in FIGS. 4 and 5. As shown in FIG. 4, with a current of 1.95 mA, the pressure within the fluid line 50 can be estimated to be approximately 0 psi. As shown in FIG. 5, with a current of 7.61 mA, the pressure within the fluid line 50 can be estimated to be approximately 40 psi. The correlation between the current and the pressure within the fluid line 50 may be determined via testing using a pressure sensor to measure the pressure within the fluid line 50.

Figure 7:
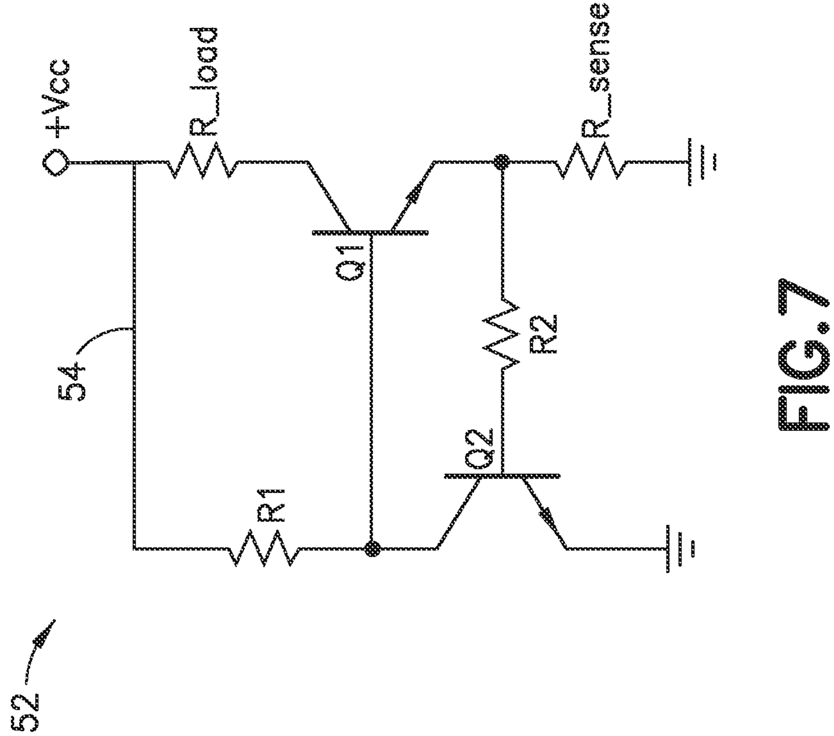
FIG. 7 is a schematic of a current limiting circuit according to a second aspect or embodiment of the present application.
Figure 6:
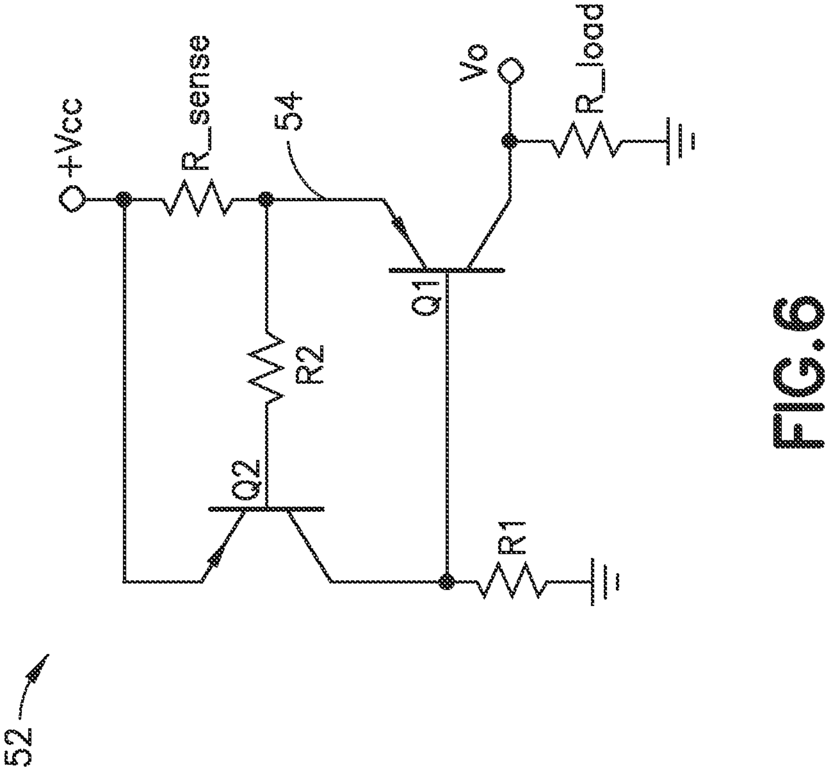
FIG. 6 is a schematic of a current limiting circuit according to one aspect or embodiment of the present application.
Figure 8:
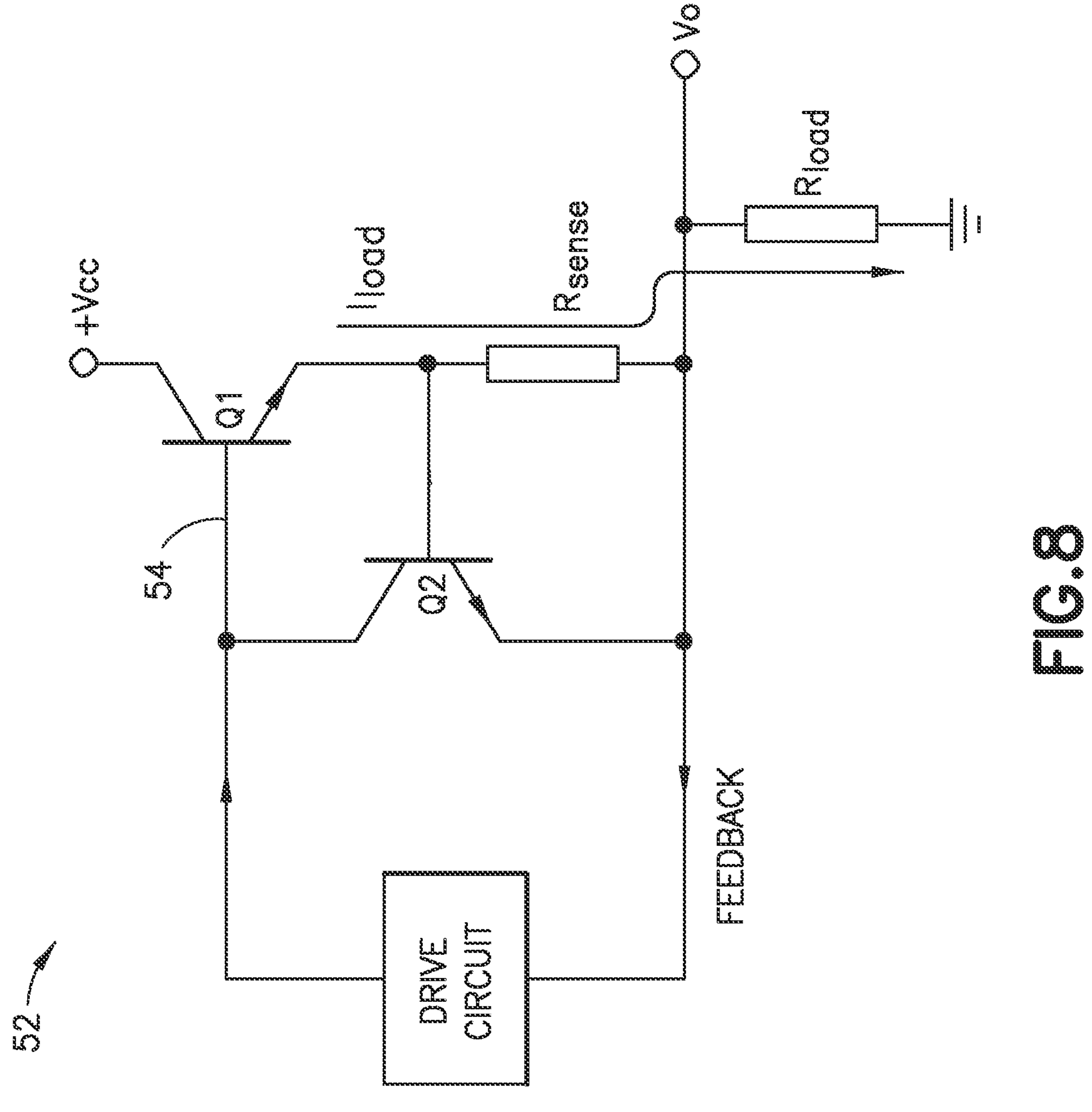
FIG. 8 is a schematic of a current limiting circuit according to a third aspect or embodiment of the present application.
Figure 9:
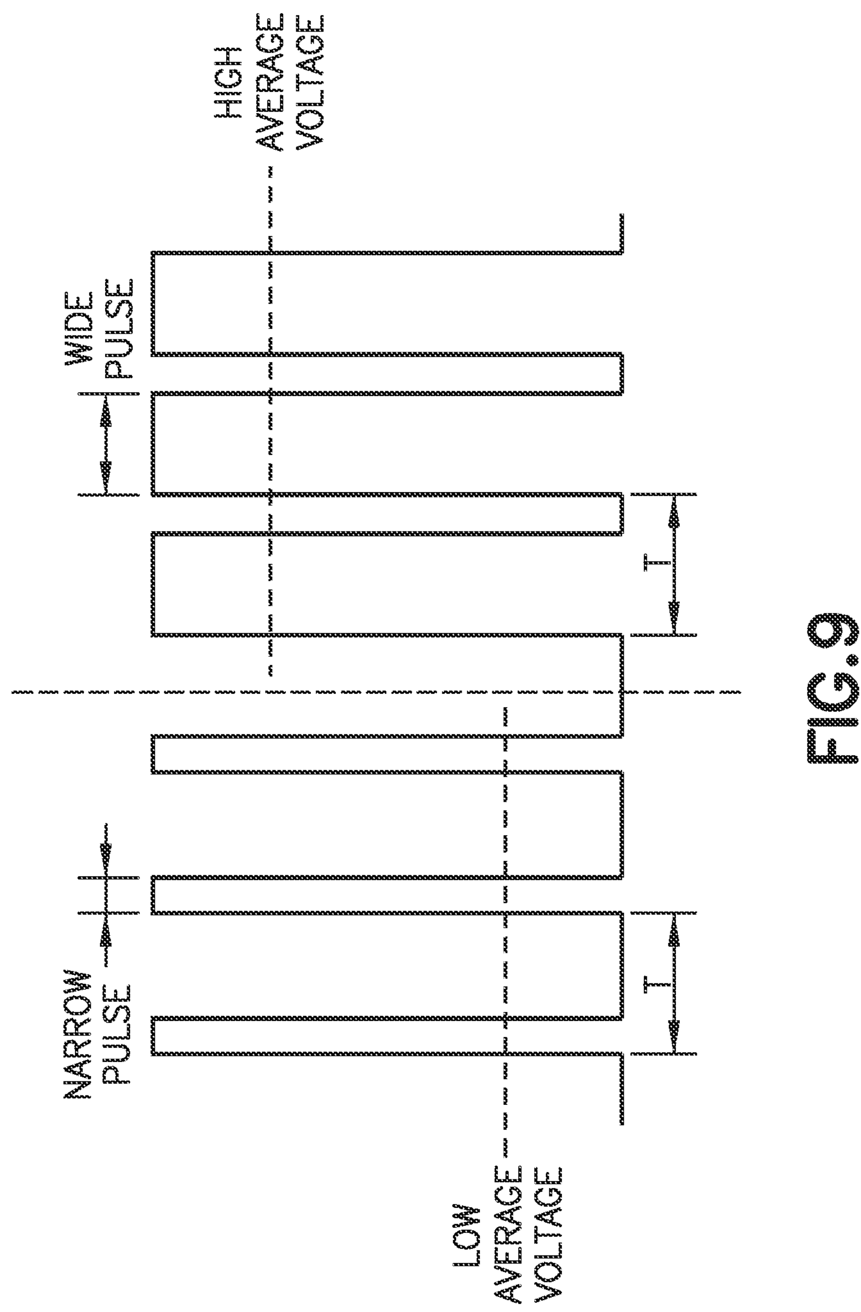
FIG. 9 is a schematic of a method of modulating power according to a further aspect or embodiment of the present application.

Referring to FIGS. 6-9, in one aspect or embodiment, the drug delivery device 10 includes a power limitation subsystem 52 configured to limit a power level supplied to the pump and valve mechanism 42. As shown in FIGS. 6-8, the power limitation subsystem 52 may be a current limiter subsystem 54. The current limiter subsystem 54 is configured to limit or cap the current supplied to the pump and valve mechanism 42. The current limiter subsystem 54 may utilize PNP transistors (FIG. 6) and/or NPN transistors (FIGS. 7 and 8). In a further aspect or embodiment, the power limitation subsystem 52 is provided by the microcontroller 24 modulating a voltage supplied to the pump and valve mechanism 42. As shown in FIG. 9, by using pulse width modulation, the power supplied to the pump and valve mechanism 42 can be modulated. For example, using a narrow pulse over a period of time will result in a lower average voltage than using a wider pulse over a period of time. The pulse width modulated signal may be smoothed by using dedicated circuitry such as capacitors, or may be smoothed by the load formed by the actuator itself.

In one aspect or embodiment, the power limitation subsystem 52 is configured to be adjustable to allow the power level supplied to the pump and valve mechanism 42 to be varied as needed. In one aspect or embodiment, the power limitation subsystem 52 has an activated mode where the power level being supplied is limited and a deactivated mode where the power level being supplied is not limited. The activated mode and the deactivated mode may be provided via additional circuitry and/or by the control via the microcontroller 24.

Figure 11:
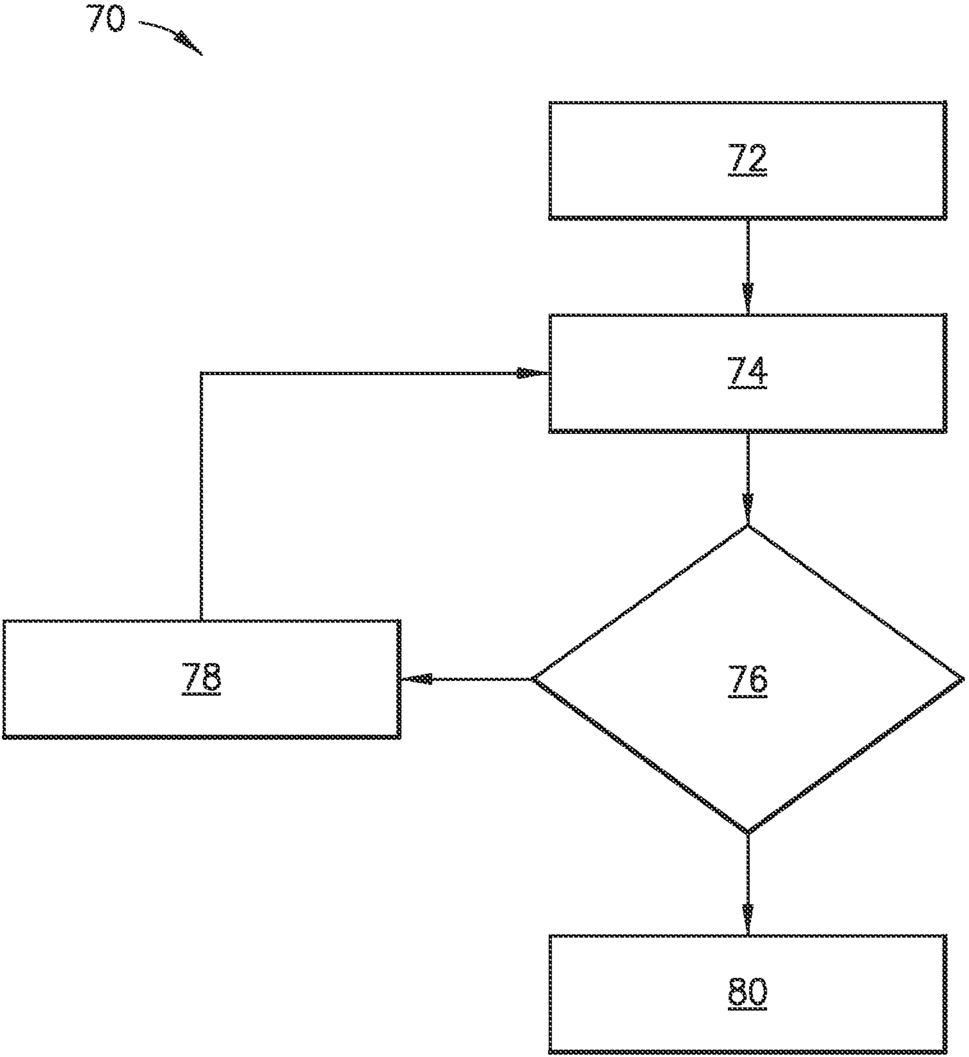
FIG. 11 is a schematic of a method of power management for drug delivery device according to one aspect or embodiment of the present application.

Referring to FIG. 11, in one aspect or embodiment, a method 70 of pressure management for the drug delivery device 10 includes: delivering fluid 72 through the fluid line 50 via the pump and valve mechanism 42 at a first power level; detecting 74 a pressure within the fluid line 50; determining 76 whether the pressure within the fluid line 50 exceeds a high pressure threshold level; delivering fluid 78 through the fluid line 50 via the pump and valve mechanism 42 at a second power level until a predetermined condition is satisfied, where the second power level is lower than the first power level; and resuming 80 the delivery of the fluid through the fluid line 50 at the first power level after the predetermined condition is satisfied. In one aspect or embodiment, the predetermined condition is a predetermined pressure level within the fluid line. The second power level may be provided via the current limiter subsystem 54, as discussed above. The second power level may also be provided by modulating the voltage supplied to the pump, as discussed above.

Figure 10A:
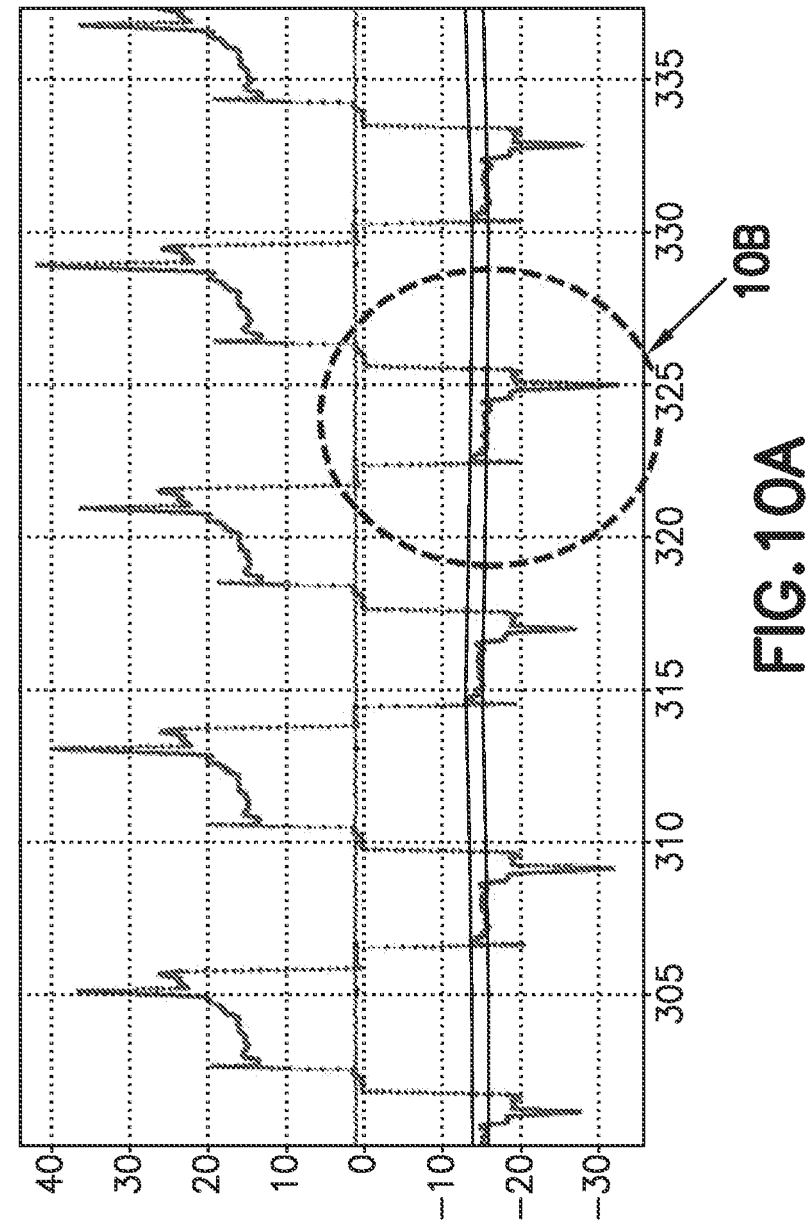
FIG. 10A is a graph of current versus time for the drug delivery device of FIG. 1, showing a method of determining fluid path pressure according to one aspect or embodiment of the present application.
Figure 10B:
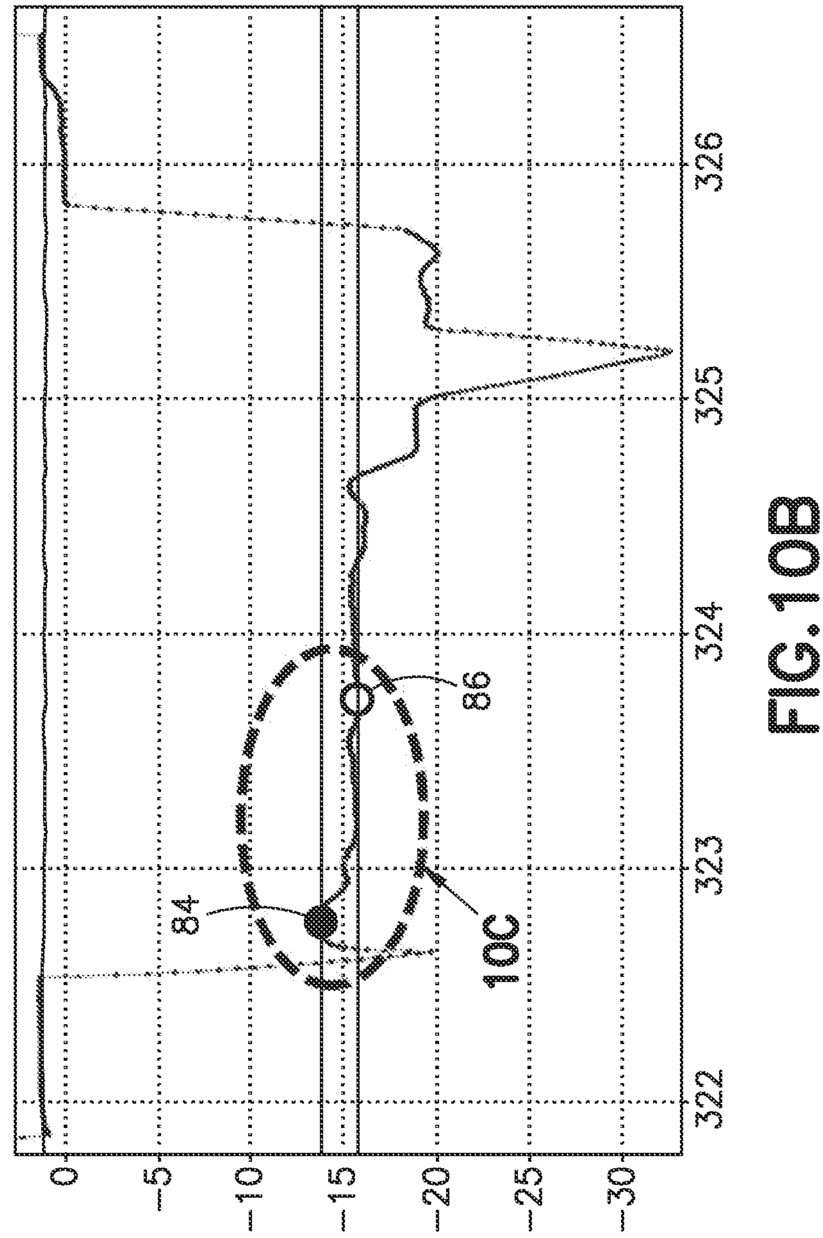
FIG. 10B is an enlarged graph of area 10B shown in FIG. 10A.
Figure 10C:
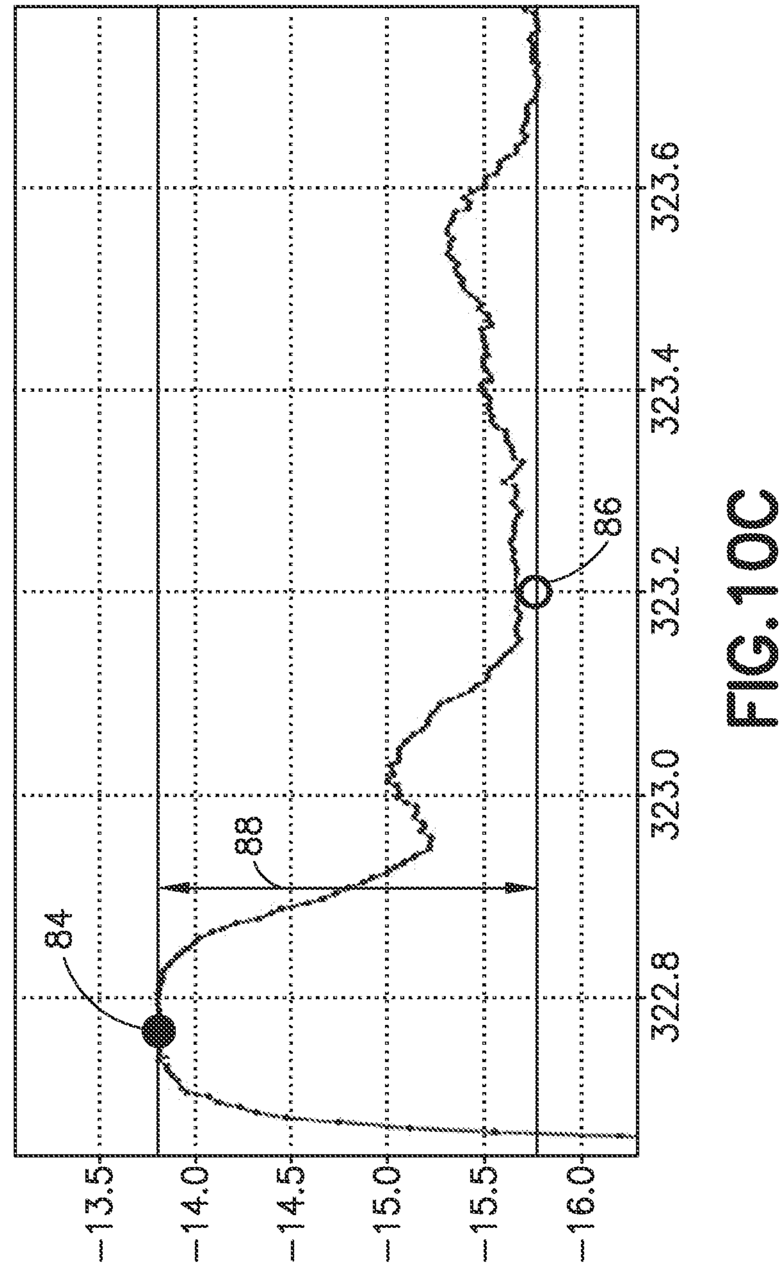
FIG. 10C is an enlarged graph of area 10C shown in FIG. 10B.

Referring to FIGS. 10A-10C, in one aspect or embodiment, the pressure within the fluid line 50 is detected by measuring a current of the drug delivery device 10 during actuation of the pump and valve mechanism 42. In one aspect or embodiment, the current is measured by measuring a voltage drop across a resistor. The measuring of the current of the drug delivery device 10 includes subtracting a reference or baseline current value 84 from a peak current value 86 during an actuation cycle of the pump and valve mechanism 42 to determine a stroke current value 88, although other suitable current detection arrangements may be utilized. The stroke current value 88 is utilized to estimate the downstream pressure of the fluid line 50 for the particular actuation cycle of the pump and valve mechanism 42. For example, the stroke current value 88 can be corresponded to various downstream pressure levels through testing or benchmarking such that the stroke current value 88 can be used to accurately estimate the pressure level of the fluid line 50.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

The invention claimed is:

1. A method of pressure management for a drug delivery device comprising electronics circuitry, a reservoir, a pump, a fluid line, and a power source, the method comprising:

delivering fluid through the fluid line via the pump at a first power level;

detecting a pressure within the fluid line by measuring a current of the drug delivery device during actuation of the pump;

determining whether the pressure within the fluid line exceeds a high pressure threshold level;

delivering fluid through the fluid line via the pump at a second power level until a predetermined condition is satisfied, the second power level is lower than the first power level and the second power level is provided by modulating the voltage supplied to the pump; and resuming the delivery of the fluid through the fluid line at the first power level after the predetermined condition is satisfied.

2. The method of claim 1, wherein the predetermined condition comprises a predetermined pressure level within the fluid line.

3. The method of claim 1, wherein the second power level is provided via a current limiter subsystem.

4. The method of claim 3, wherein the current limiter subsystem comprises transistors or an operational amplifier.

5. The method of claim 1, wherein the pressure within the fluid line is detected by measuring a current of the drug delivery device during actuation of the pump.

6. The method of claim 5, wherein the measuring of the current of the drug delivery device comprises subtracting a reference current value from a peak current value during an actuation cycle of the pump to determine a stroke current value.

7. A computer program product for a method of pressure management for a drug delivery device comprising a microcontroller, a reservoir, a pump, a fluid line, and a power source, the computer program product comprising at least one non-transitory computer-readable medium including program instructions that, when executed by the microcontroller, cause the drug delivery device to:

deliver fluid through the fluid line via the pump at a first power level;

detect a pressure within the fluid line by measuring a current of the drug delivery device during actuation of the pump;

determine whether the pressure within the fluid line exceeds a high pressure threshold level;

deliver fluid through the fluid line via the pump at a second power level until a predetermined condition is satisfied, the second power level is lower than the first power level, wherein the at least one non-transitory computer-readable medium further includes program instructions that, when executed by the microcontroller, cause the microcontroller to modulate voltage supplied to the pump to provide the second power level; and resume the delivery of the fluid through the fluid line at the first power level after the predetermined condition is satisfied.

8. The computer program product of claim 7, wherein the predetermined condition comprises a predetermined pressure level within the fluid line.

9. The computer program product of claim 7, wherein the at least one non-transitory computer-readable medium further includes program instructions that, when executed by the microcontroller, cause the drug delivery device to:

measure the current of the drug delivery device during actuation of the pump to detect the pressure within the fluid line.

10. The computer program product of claim 9, wherein the measuring of the current of the drug delivery device comprises subtracting a reference current value from a peak current value during an actuation cycle of the pump to determine a stroke current value.

11. A method of pressure management for a drug delivery device comprising electronics circuitry, a reservoir, a pump, a fluid line, and a power source, the method comprising:

moving the cannula from a retracted position positioned within the device to an extended position where a cannula extends outside of the device;

delivering fluid through the fluid line via the pump at a first power level;

detecting a pressure within the fluid line;

determining whether the pressure within the fluid line exceeds a high pressure threshold level;

delivering fluid from the reservoir to the cannula through the fluid line via the pump at a second power level until a predetermined condition is satisfied, the second power level is lower than the first power level and the second power level is provided by modulating the voltage supplied to the pump; and resuming the delivery of the fluid through the fluid line at the first power level after the predetermined condition is satisfied.

* * * * *